United States Patent

Kitaya et al.

[11] Patent Number: 4,647,197
[45] Date of Patent: Mar. 3, 1987

[54] DISTORTION INSPECTION APPARATUS OF A GLASS PLATE

[75] Inventors: Katsuhiko Kitaya, Tokyo; Nagayoshi Ichise, Fukui, both of Japan

[73] Assignee: Nippon Sheet Glass Co., Ltd., Japan

[21] Appl. No.: 674,608

[22] Filed: Nov. 26, 1984

[30] Foreign Application Priority Data

Jan. 12, 1983 [JP] Japan .................. 58-227598

[51] Int. Cl.$^4$ .......................................... G01N 21/88
[52] U.S. Cl. ................................ 356/239; 250/563; 250/572; 358/406
[58] Field of Search .................. 356/239, 384, 387; 250/562, 563, 572; 358/106; 364/507, 525

[56] References Cited

U.S. PATENT DOCUMENTS

| | | | |
|---|---|---|---|
| 2,871,756 | 2/1959 | Graves et al. | 356/239 X |
| 3,688,235 | 8/1972 | Migeotte | 356/239 |
| 4,076,426 | 2/1978 | Gross et al. | 356/239 |
| 4,310,242 | 1/1982 | Genco et al. | 356/239 X |
| 4,461,570 | 7/1984 | Task et al. | 356/239 |

FOREIGN PATENT DOCUMENTS 1308013 9/1962 France .................. 356/239

*Primary Examiner*—Vincent P. McGraw
*Assistant Examiner*—Matthew W. Koren
*Attorney, Agent, or Firm*—McDougall, Hersh & Scott

[57] ABSTRACT

In a distortion inspection apparatus of a glass plate, a light and dark contrast pattern is sensed by an image sensor through a glass plate. The number of bits corresponding to a light or dark portion is detected from bipolar image data which are divided into a plurality of bits along each of parallel scanning lines assumed upon a surface of the glass plate. Then, a distortion state of the surface of the glass plate is discriminated in accordance with the differences among the thus detected number of bits and a reference value thereof. In such an arrangement, quantitative distortion discrimination can be performed.

15 Claims, 9 Drawing Figures

DISTORTION INSPECTION APPARATUS OF A GLASS PLATE

BACKGROUND OF THE INVENTION

1. Field of the Invention

The present invention relates to a distortion inspection apparatus for glass plate and, more particularly, to an apparatus for optical distortion inspection of reinforced curved glass or laminated curved glass such as a windshield glass of a vehicle.

2. Description of the Prior Art

A so-called reinforced curved glass or laminated curved glass in which a plurality of glass sheets are adhered by means of resin layers such as polyvinyl butyral is used as windshield glass of an automobile. In such glass windshields, optical distortions or uneven surfaces can occur. When the distortion or abraded surface is considerable, the field of vision can be undesirably distorted according to the angle of sight.

Conventionally, an examiner utilizing a light and dark stripe pattern (e.g., a zebra-like pattern) from a distant position visually inspects a completed laminated glass windshield and thus performs organoleptic inspection of the the stripe pattern distortion while the viewing angle (azimuth) of the windshield is changed, thereby examining or discriminating the quality of the laminated glass. However, in such a visual inspection, quantitative standardization cannot be obtained, and differences among examiners prevent uniform inspection quality.

SUMMARY OF THE INVENTION

The present invention has been made in consideration of the above situation, and has as its object to provide an inspection apparatus in which quantitative standardization and automatic determination can be performed and a quality of a glass plate can be improved by highly precise distortion inspection.

In a distortion inspection apparatus of a glass plate according to the present invention, a light and dark contrast pattern is sensed by an image sensor through a glass plate. The number of bits corresponding to a light or dark portion is detected from image data which are divided into a plurality of bits along parallel scanning lines assumed upon a surface of the glass plate. Then, a distortion state of the surface of the glass plate is discriminated in accordance with the differences among the thus detected number of bits and a reference value thereof. In such an arrangement, quantitative distortion discrimination can be performed.

DETAILED DESCRIPTION OF THE PREFERRED EMBODIMENT

An embodiment according to the present invention will be described hereinafter.

Figure 1:
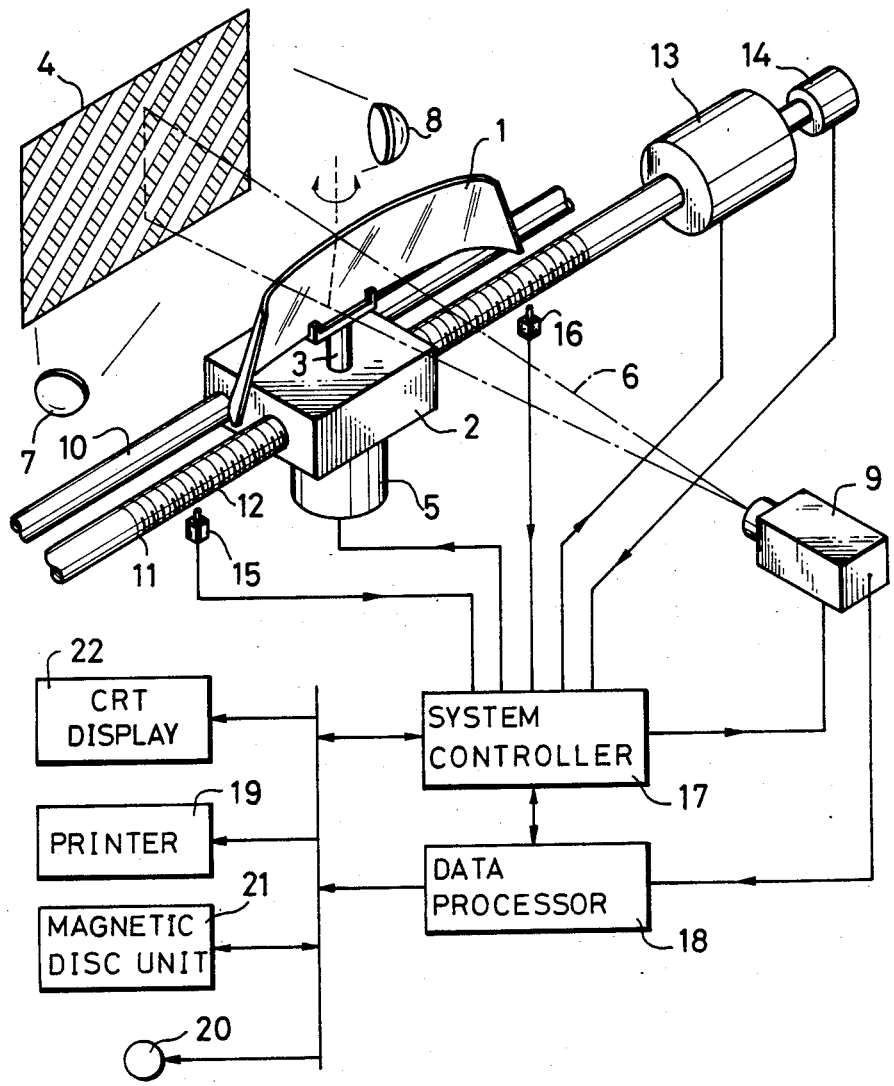
FIG. 1 is a representation schematically showing a distortion inspection apparatus of a glass plate according to an embodiment of the present invention.

FIG. 1 is a representation schematically showing a distortion inspection apparatus of a windshield glass of a vehicle according to an embodiment of the present invention. In FIG. 1, a windshield glass 1 is mounted on a leading end of a rotating shaft 3 of a table 2 so as to have substantially the same inclination as when mounted on a vehicle and opposed to a zebra pattern board 4 having a black and white stripe pattern corresponding to an outer field of view. Hatched portions of the zebra pattern 4 of FIG. 1 correspond to black portions and other portions correspond to white portions. The rotating shaft 3 is driven by a motor 5. A horizontal rotating position of the rotating shaft 3 is controlled such that a surface of the windshield glass 1 forms a predetermined angle with respect to an inspection optical path 6. Light sources 7 and 8 are arranged at the front surface side of the zebra pattern board 4. The optical path 6 is formed so that reflected light from the pattern board 4 is irradiated into a CCD camera 9 through the windshield glass 1.

The table 2 is supported by two parallel guide rods 10 and 11 slidable along a direction perpendicular to the optical path 6, thereby moving the windshield glass 1 parallel to the pattern board 4. A conveyor threaded portion 12 is formed on one of the guide rods 10 and 11. When the guide rod 11 with the threaded portion 12 is rotated by a motor 13, the windshield glass 1 is moved in a horizontal direction together with the table 2. The horizontal moving distance is measured in accordance with an output pulse from a pulse generator 14 coaxially mounted on a shaft of the motor 13. In order to detect start and end points of horizontal movement of the table 2, position sensors 15 and 16 are provided along a moving path of the table 2.

Sensor outputs of the position sensors 15 and 16 and the pulse generator 14 are supplied to a system controller 17. Control of horizontal movement and rotation angle of the windshield glass 1 and drive of the CCD camera 9 are performed in accordance with these sensor outputs and a program of the system controller 17. An output of the CCD camera 9 is supplied to a data processor 18, and discrimination of an optical distortion state of the windshield glass 1 is performed in accordance with a data processing procedure to be described later. The discrimination result is printed by a printer 19 in a data format showing distortion distribution of the glass surface. When a defective windshield glass 1 is detected, an alarm 20 is operated. Reference discrimination data is stored in a magnetic disc unit 21 for each type of windshield glass 1 and is read out when distortion discrimination is performed. The operation program of the system of FIG. 1 and data for monitoring the operation are displayed on a CRT display 22.

Figure 2:
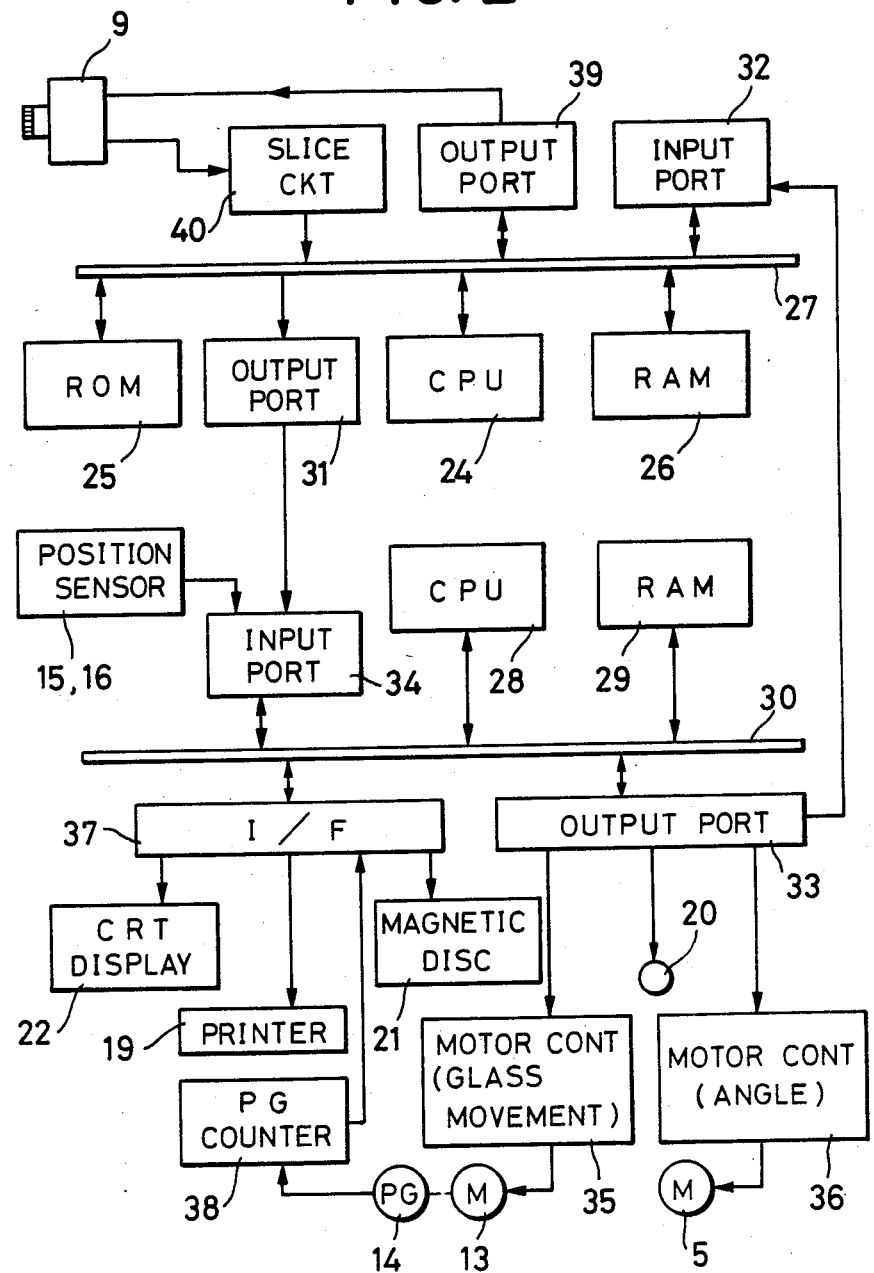
FIG. 2 is a block diagram of a system controller and a data processor shown in FIG. 1.

FIG. 2 is a block diagram showing the system controller 17 and the data processor 18 (FIG. 1) in more detail. Processing and discrimination of inspection data are mainly performed by a microcomputer consisting of a CPU 24, a ROM 25, a RAM 26 and a data bus 27, and control of components of this system (e.g., a glass moving motor controller 35, a glass angle setting motor controller 36, the printer 19, the magnetic disc unit 21, the CRT display 22 and the like) is performed by a second microcomputer consisting of a CPU 28, a RAM 29 and a data bus 30. The microcomputers are coupled to each other through an output port 31, an input port 32, an output port 33 and an input port 34, and communicate with each other.

Figure 3A:
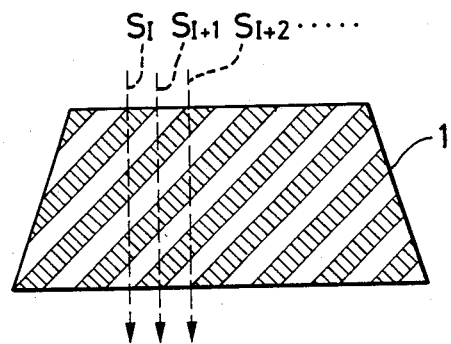
FIGS. 3A and 4A are schematical views of windshield glasses showing transmitted images of light and dark patterns, respectively.
Figure 4A:
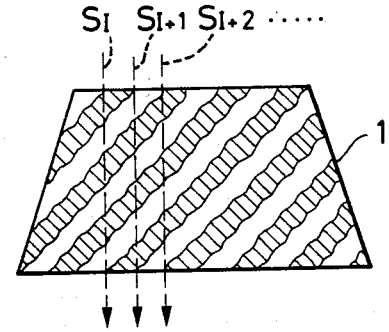

FIGS. 3A and 4A are views respectively showing a distortion state of an image when the zebra pattern board 4 is viewed through the windshield glass 1. The black and white stripe patterns of the zebra pattern board 4 respectively have, for example, a 25 mm width and 50 mm pitch inclined at 45°. When this pattern is viewed through from the front side of the windshield glass 1, a normal transmitted image as shown in FIG. 3A can be obtained. However, when the windshield glass 1 is rotated through a predetermined angle (e.g., a standard inspection angle of 45°) by the motor 5 of FIG. 1, characteristics due to any distortion of the glass surface become obviously apparent and a transmitted image having a disturbed waveform as shown in FIG. 4A is obtained. Note that rotating the windshield glass 1 in the horizontal plane corresponds to a view obtained by a driver of a vehicle when he looks to his right or left front (i.e., pavement side).

The CCD camera 9 serves as a line sensor, and converts light and dark image data sensed along a plurality of scanning lines S assumed for the vertical direction as shown in FIGS. 3A and 4A into an electric signal. Resolving power of the CCD camera 9 is 2,048 bits per scanning line. The distance between two adjacent scanning lines is 10 mm on the surface of the windshield glass 1. This distance is formed by horizontal movement of the windshield glass 1 by the motor 13. The pulse generator 14 which is coupled to the motor 13 generates a pulse at an output rate of 1 mm. This pulse output is supplied to a PG counter 38 (FIG. 2) and a horizontal movement position of the windshield glass 1 is measured. Output data of the counter 38 is supplied to the CPU 28 through an interface 37, and image outputs of the respective scanning lines for every 10-mm horizontal movement are fetched by the microcomputer.

Figure 3B:
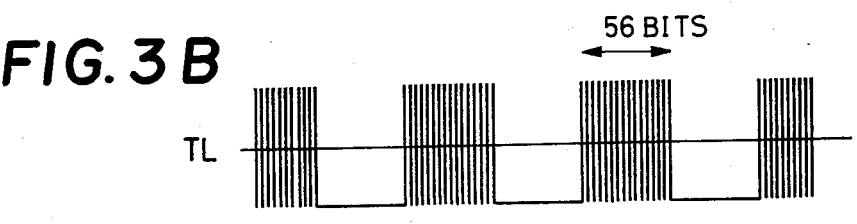
FIGS. 3B and 4B are waveform charts corresponding to the transmitted images shown in FIGS. 3A and 4A.
Figure 4B:
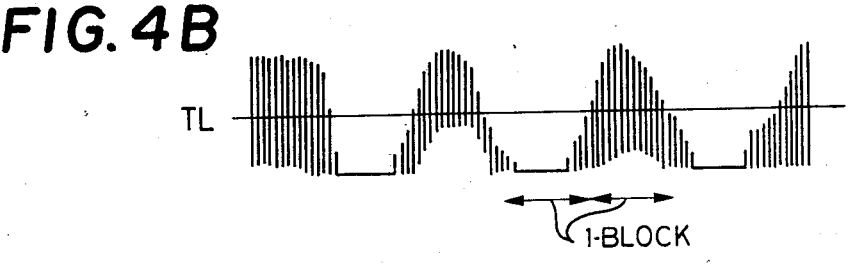

The image output of the CCD camera 9 is a signal having a level (the bright portion is high level) corresponding to a transmitted pattern, as shown in FIG. 3B or 4B. A read-out clock of 2,048 bits from the output port 39 is supplied to the CCD camera 9 for every 10 mm of horizontal movement. When the CCD camera 9 senses the normal transmitted image shown in FIG. 3A, a signal in which high and low levels alternately appear for every 56 bits is received corresponding to the bright and dark portions of the pattern, as shown in FIG. 3B. This coincides with a theoretical value: 25 mm (pattern width) ÷ sin 45°(pattern angle)×2,048 bits÷1,300 mm (longitudinal length of the pattern board)=56 bits.

However, when the transmitted image having much distortion as shown in FIG. 4A is sensed by the CCD camera 9, the respective pattern widths along the scanning lines are increased or decreased in accordance with the distortion and the boundary between the adjacent light and dark portions becomes indistinct, thus obtaining a signal as shown in FIG. 4B.

The output of the CCD camera 9 is supplied to a slice circuit 40. When the output from the CCD camera 9 is higher than a constant threshold level TL shown in FIGS. 3B and 4B, it is discriminated to be logic "1" by the circuit 40, and when the output is lower than the threshold level TL, it is discriminated to be logic "0". This data is temporarily stored in the RAM 26, and is then processed by the CPU 24 according to the data processing procedures to be described later. Thus, optical distortion or uneven surface of the glass surface is discriminated. The CPU 24 determines whether or not the number of bits of "1" or "0" values falls within the range of the reference value 56 bits ±α (α is a tolerance of specification) for every black or white stripe, thus performing the discrimination operation.

Figure 5A:
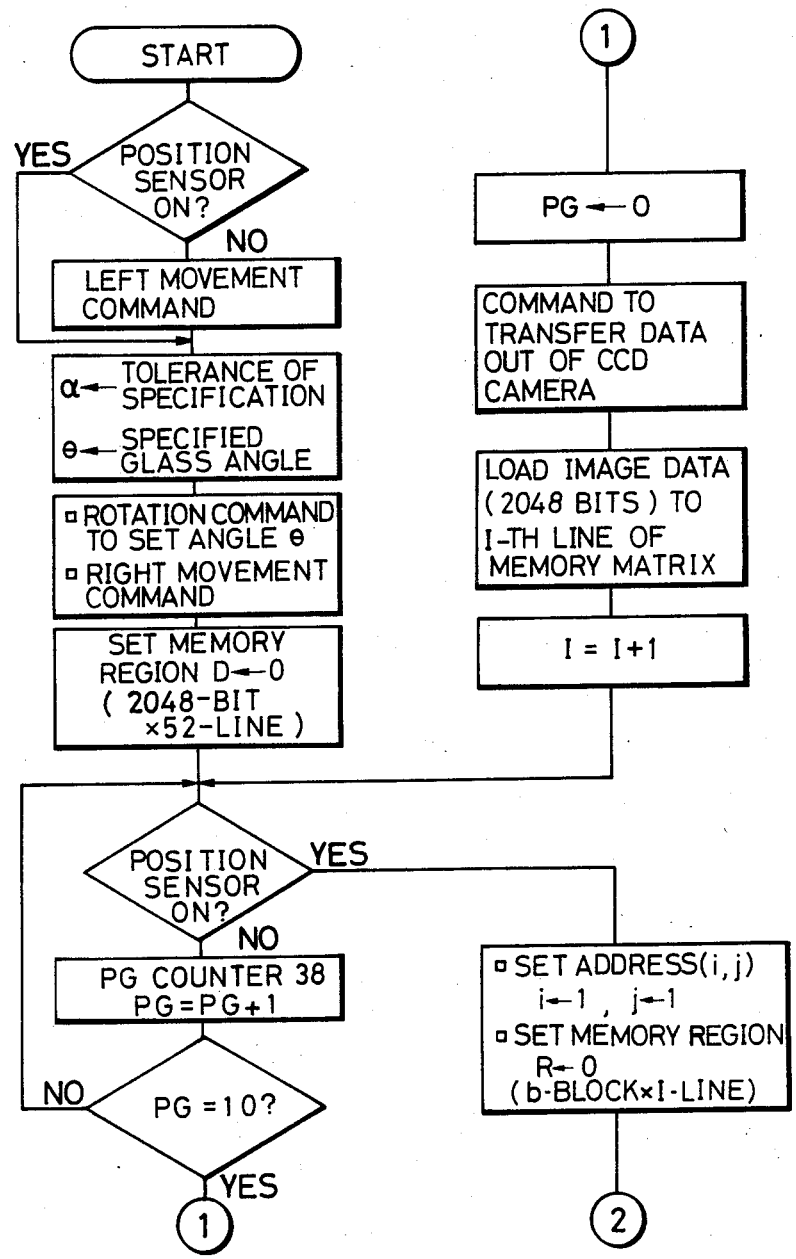
FIGS. 5A and 5B are flow charts respectively showing procedures of data processing of distortion discrimination.
Figure 5B:
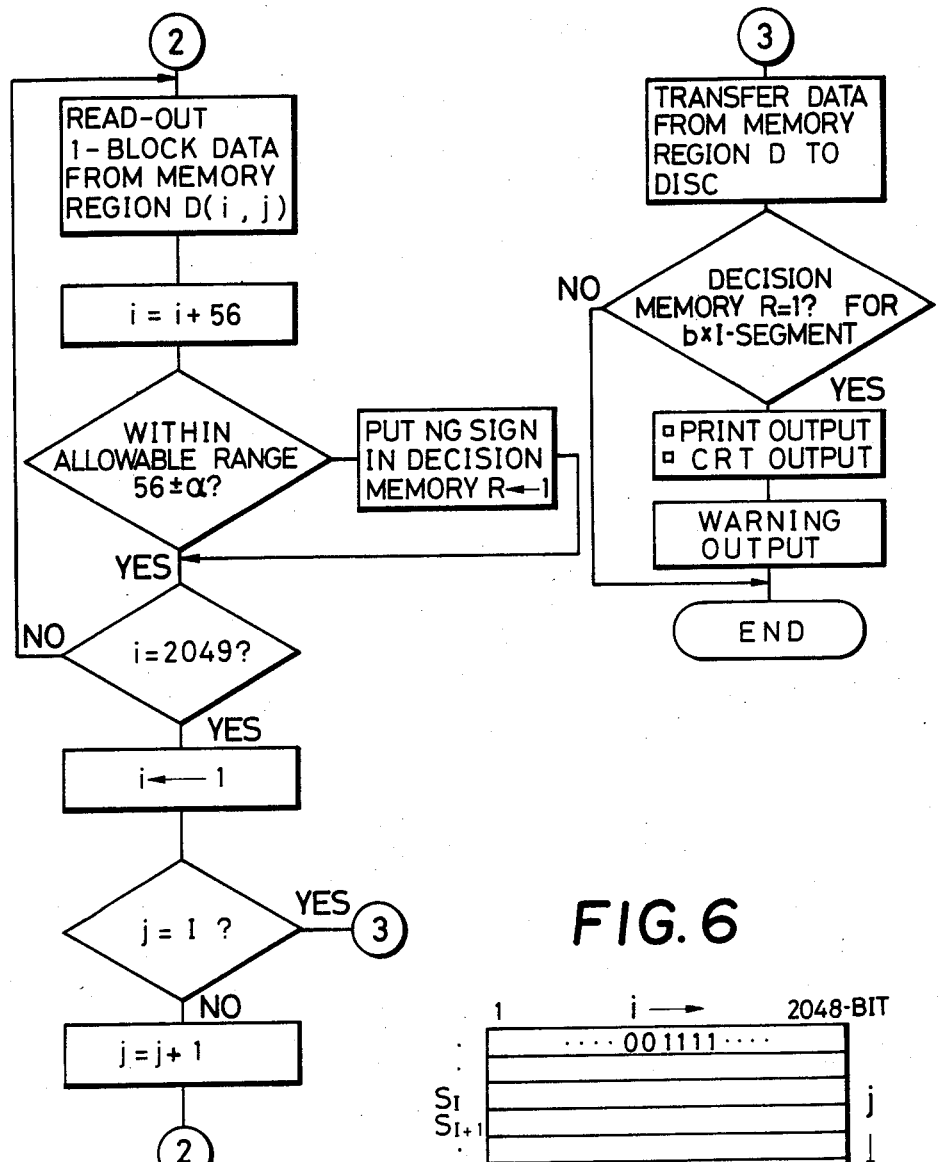

FIGS. 5A and 5B are flow charts showing the data processing procedures. A left movement command of the table 2 by the motor 13 is generated to the motor controller 35 until the position sensor 15 is turned on. Then, the tolerance α and a specified glass angle ¼ (e.g., 45°) are respectively set. The tolerance is stored in the magnetic disc unit 21 for every kind of windshield 1. A rotation command of the windshield glass 1 by the motor 5 is supplied to the motor controller 36 and a right movement command is supplied to the motor controller 35, thereby starting horizontal movement of the windshield glass 1 to the right. Simultaneously, in the RAM 26, a memory region D of 2,048 bits×52 lines is initialized.

The right movement position of the windshield glass 1 is measured by a count of the PG counter 38. Every time the count PG of the counter 38 reaches 10 (moving length 10 mm), a command for fetching the image data from the CCD camera 9 is generated. The image data having 2,048 bits is transmitted to an Ith line of the memory region D corresponding to one scanning line $S_I$ shown in FIG. 3A or 4A. The same data fetching operation as described above is performed for the next scanning line $S_{I+1}$. Thus, when the position sensor 16 at the right end is turned on, the memory region D of 2,048 bits×the total number of the scanning lines is obtained. A maximum value of "I" of 52 lines is obtained.

When the image data fetching operation for the overall glass surface is completed, the discrimination operation of the distortion state is performed. In order to access the data stored in the memory region D of FIG. 6, addresses i (bit addresses along the scanning line) and j (line addresses representing the scanning line number) are respectively reset to an initial value "1". It should be noted that the CCD camera 9 always senses a predetermined position of the pattern board 4 and a first leading edge of the image signal of each scanning line coincides with the initial value "1" of the bit address. Another memory region R (b block×I lines) for storing the discrimination result is then prepared. As shown in FIGS. 3B and 4B, one block of data consists of 56 bits. The image data having no distortion includes data of high level "1" or low level "0" for 56 bits in each block.

Figure 6:
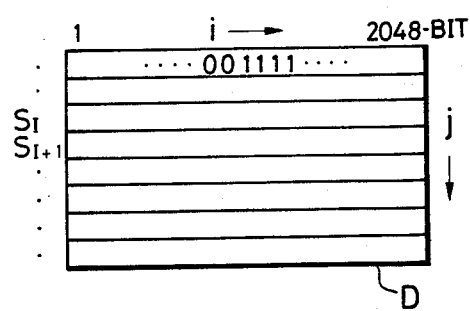
FIG. 6 is a representation showing a data memory area.

While the address is changed up to i+56, 56 image data are fetched from the memory region D of FIG. 6 and it is checked whether the total number of the data "1" or "0" falls within the range of 56 (standard value) ±α (tolerance). When the number falls outside this range, an NG sign "1" representing a defective product is stored at a corresponding address of the memory region R for storing the discrimination result. The discrimination data processing is performed for every block until the bit address i reaches 2,049 by one line address j. Furthermore, while the line address j is updated by one, the discrimination operation is sequentially performed for all the blocks in the memory region D.

When the line address j reaches the total number I of the scanning line, the discrimination operation ends and the discrimination result is generated. In order to keep the inspection data, all the data stored in the memory region D is supplied to the magnetic disc unit 21. The memory region R (b block×I lines) is accessed. When the data "1" (defective portion) is detected, an output signal for the pattern displaying the defective portion is generated to the printer 19 and the CRT display 22. The alarm 20 is also operated.

The present invention has been described with reference to the embodiment hereinabove. However, various changes and modifications may be made within the spirit and scope of the present invention. For example, image data of a transmitted image of the windshield glass which satisfies desired specifications are stored as reference data, and these data is compared with image data of an object to be inspected. Thus, the number of coincidences or variations between the inspection data and the reference data is detected at each corresponding bit position, and the extent of the distortion can be discriminated in accordance with this number. This discrimination operation can be performed for every block or every scanning line. Meanwhile, in FIG. 1, the windshield glass 1 is fixed and the CCD camera 9 can be horizontally moved. In the CCD camera 9, a line sensor of MOSFET type or photodiode-array type can be used. If a surface sensor of matrix type is used instead, relative movement of the windshield glass 1 or the CCD camera 9 can be omitted.

As described above, the number of bits corresponding to a bright or dark portion is detected for each of a plurality of areas which are defined by dividing a light and dark pattern along vertical scanning lines assumed upon a glass sheet in accordance with image data of the light and dark pattern which is sensed through the glass sheet, and a distortion state of the glass plate is discriminated in accordance with a difference between the thus obtained number of bits and a reference value. For this reason, quantitative discrimination of the state of distortion or surface unevenness can be performed, and yield and quality of the glass sheet can be improved by stable, high-precision inspection.

What is claimed is:

1. A distortion inspection apparatus of a glass plate comprising: a light and dark stripe pattern in which bright and dark portions of the pattern are alternately arranged; image sensing means for sensing images of the pattern viewed through said glass plate so as to obtain image data corresponding to said light and dark stripe pattern for each of a plurality of parallel scanning lines assumed upon a surface of the glass plate said image data consisting of a plurality of bit images; detecting means for detecting the number of bits of said image data representing widths of the bright or dark portion along each scanning line; and discriminating means for discriminating a distortion state of the glass plate with reference to a difference between the number of bits detected by said detecting means and a reference value corresponding to a predetermined number of bits.

2. An apparatus according to claim 1, wherein said image sensing means comprises a line sensor for obtaining the image data which correspond to one of the scanning lines, and moving means for relatively moving one of the glass plate and said line sensor along a direction perpendicular to the scanning lines.

3. An apparatus according to claim 1, wherein the image data is bipolar data in which one of the bright and dark portions corresponds to logic level "1" and the other of the bright and dark portions corresponds to logic level "0".

4. An apparatus according to claim 2, wherein said image sensing means comprises a slice circuit for discriminating an amplitude of an output signal from said line sensor at a predetermined threshold level so as to obtain bipolar image data having logic levels "1" and "0".

5. An apparatus according to claim 2 or 4, wherein said line sensor is a charge coupled device, and the image data is obtained for each bit of a predetermined number of bits corresponding to a transfer clock pulse array of said charge coupled device.

6. An apparatus according to claim 1 or 2, wherein said image sensing means comprises rotating means for changing an angle of a surface of the glass plate with respect to an inspection optical path which couples said light and dark stripe pattern to an image sensor.

7. An apparatus according to claim 2, wherein said moving means comprises a carriage which is arranged so as to move the glass plate along a horizontal direction, a feeding threaded portion which is coupled to said carriage and a feeding motor, and the scanning lines are assumed along substantially a vertical direction.

8. An apparatus according to claim 7, wherein said carriage comprises a rotating shaft, which supports the glass plate and is arranged along the vertical direction and rotation driving means of said rotating shaft, so that the angle of the surface of the glass plate is changed with respect to the inspection optical path which couples said light and dark stripe pattern and said line sensor.

9. An apparatus according to claim 2, wherein said moving means comprises generating means for generating a timing pulse which determines a position of each of said scanning lines on the surface of the glass plate in the course of feeding operation thereof, thereby forming parallel scanning lines at predetermined intervals on the sufface of the glass plate.

10. An apparatus according to claim 1, 2 or 3, wherein said detecting means comprises memory means for storing the image data for every scanning line by a predetermined number of bits.

11. An apparatus according to claim 10, wherein said detecting means further comprises addressing means for reading out the image data from said memory means for every unit block which includes a reference bit number in correspondence with the bright or dark portion of a reference image data, and counting means for counting the number of bits corresponding to the bright or dark portion in the image data read out for every unit block; and said discriminating means comprises comparing means for comparing the reference bit number and the counted bit number.

12. An apparatus according to claim 11, wherein said comparing means comprises means for comparing the counted bit number and a tolerance range of specification which is determined by the reference bit number ±α (α is a tolerance), and for generating an "NG" sign when a comparison result falls outside the tolerance range.

13. An apparatus according to claim 12, further comprising storing means for storing the "NG" sign for every unit block of the scanning lines, and display means for pattern-displaying a content of said storing means so as to correspond to the surface of said glass plate or printing means for pattern-printing the content of said storing means so as to correspond to the surface of said glass plate.

14. An apparatus according to claim 1, wherein the glass plate is a windshield glass of a vehicle.

15. An apparatus according to claim 14, wherein the windshield glass is a laminated curved glass which is formed by adhering a plurality of glass sheet through resin layers.

* * * * *